United States Patent [19]

Wolfinger

[11] 4,207,236
[45] Jun. 10, 1980

[54] 3-(TERT-ALKYLTHIO)-1,3-THIAZOLIDIN-2,4-DIONE

[75] Inventor: Mark D. Wolfinger, Chicago, Ill.

[73] Assignee: Monsanto Company, St. Louis, Mo.

[21] Appl. No.: 12,624

[22] Filed: Feb. 16, 1979

Related U.S. Application Data

[62] Division of Ser. No. 854,092, Nov. 23, 1977, Pat. No. 4,165,417.

[51] Int. Cl.$^2$ ............................................. C07D 277/04
[52] U.S. Cl. .................................................... 548/183
[58] Field of Search .................................. 260/306.7 R

[56] References Cited

U.S. PATENT DOCUMENTS

| | | | |
|---|---|---|---|
| 3,546,185 | 12/1970 | Coran et al. | 260/79.5 |
| 3,752,824 | 8/1973 | Coran et al. | 260/326.5 |
| 3,912,749 | 10/1975 | Ashton et al. | 260/306.7 R |

FOREIGN PATENT DOCUMENTS 1345144  1/1974  United Kingdom .

*Primary Examiner*—Nicholas S. Rizzo
*Attorney, Agent, or Firm*—Larry R. Swaney

[57] ABSTRACT

Compounds of the formula

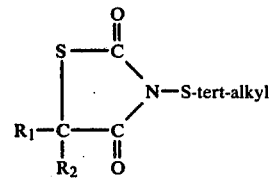

in which $R_1$ and $R_2$ independently are hydrogen, alkyl or aryl are described which compounds are potent inhibitors of premature vulcanization of rubber.

5 Claims, No Drawings

3-(TERT-ALKYLTHIO)-1,3-THIAZOLIDIN-2,4-DIONE

This is a division of application Ser. No. 854,092 filed Nov. 23, 1977, now U.S. Pat. No. 4,165,417.

This invention relates to an improved process for inhibiting premature vulcanization of rubber and to compounds which are especially potent premature vulcanization inhibitors.

BACKGROUND OF THE INVENTION

The use of sulfur derivatives of amido compounds to inhibit the premature vulcanization of vulcanizable rubber compositions is known. For example, see Coran and Kerwood, U.S. Pat. Nos. 3,546,185 and 3,752,824.

SUMMARY OF THE INVENTION

It has been discovered that tertiary-alkylthio derivatives of 1,3-thiazolidine-2,4-dione are especially potent premature vulcanization inhibitors. Surprisingly, the presence of a tertiary alkyl substituent enchances the prevulcanization inhibitor activity. The improved inhibitors of the invention are characterized by the formula

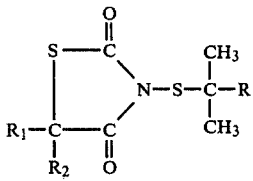

in which R is alkyl of 1-9 carbon atoms, preferably, R is alkyl of 1-5 carbon atoms, more preferably, R is methyl and $R_1$ and $R_2$ independently are hydrogen, alkyl of 1-8 carbon atoms or phenyl, preferably $R_1$ is hydrogen and $R_2$ is methyl or ethyl and, more preferably, both $R_1$ and $R_2$ are hydrogen.

Compounds of the invention may be prepared by reacting the appropriate sulfenyl chloride with 1,3-thiazolidin-2,4-dione or 5-mono- or di-substituted-1,3-thiazolidin-2,4-dione in the presence of a hydrogen chloride acceptor. Alternatively, the sulfenyl chloride may be reacted with an alkali metal salt of 5-substituted or unsubstituted 1,3-thiazolidin-2,4-dione.

Illustrative examples of compounds of the invention are:
3-(t-butylthio)-1,3-thiazolidin-2,4-dione
3-(t-hexylthio)-1,3-thiazolidin-2,4-dione
3-(t-heptylthio)-1,3-thiazolidin-2,4-dione
3-(t-octylthio)-1,3-thiazolidin-2,4-dione
3-(1,1,3,3 tetramethyl-1-butylthio)-1,3-thiazolidin-2,4-dione
3-(t-nonylthio)-1,3-thiazolidin-2,4-dione
3-(t-decylthio)-1,3-thiazolidin-2,4-dione
3-(t-dodecylthio)-1,3-thiazolidin-2,4-dione
3-(t-butylthio)-5-methyl-1,3-thiazolidin-2,4-dione
3-(t-butylthio)-5-ethyl-1,3-thiazolidin-2,4-dione
3-(t-butylthio)-5-isopropyl-1,3-thiazolidin-2,4-dione
3-(t-butylthio)-5-isobutyl-1,3-thiazolidin-2,4-dione
3-(t-butylthio)-5-pentyl-1,3-thiazolidin-2,4-dione
3-(t-butylthio)-5-hexyl-1,3-thiazolidin-2,4-dione
3-(t-butylthio)-5-heptyl-1,3-thiazolidin-2,4-dione
3-(t-butylthio)-5-octyl-1,3-thiazolidin-2,4-dione
3-(t-butylthio)-5-phenyl-1,3-thiazolidin-2,4-dione
3-(t-butylthio)-5,5-dimethyl-1,3-thiazolidin-2,4-dione
3-(t-butylthio)-5,5-diethyl-1,3-thiazolidin-2,4-dione
3-(t-butylthio)-5,5-diphenyl-1,3-thiazolidin-2,4-dione The inhibitors of the invention are incorporated into rubber stocks by mixing on a mill or in an internal mixer such as a Banbury mixer. However, the inhibitors may be incorporated by addition to latex, if desired. The process of the invention is particularly applicable to sulfur-vulcanizable rubber compositions which rubber compositions contain a sulfur vulcanizing agent such as an amine disulfide or a polymeric polysulfide but preferably, the vulcanizing agent is elemental sulfur. Rubber compositions containing organic accelerating agents are particularly improved by the inhibitors of the invention. Any organic accelerating agents which accelerate the sulfur vulcanization of rubber is satisfactory in the practice of this invention. Examples of suitable accelerators are described in U.S. Pat. No. 3,546,185, col. 9, lines 53-75 and in U.S. Pat. No. 3,780,001, col. 4, lines 43-72. The process of the invention is applicable to a wide variety of natural and synthetic rubbers and mixtures thereof. Examples of satisfactory diene rubbers are described in U.S. Pat. No. 3,546,185, col. 10, lines 15-21 and U.S. Pat. No. 3,780,001, col. 5, lines 5-33. The vulcanizable composition may also contain conventional compounding ingredients such as reinforcing pigments, extenders, processing oils, antidegradants and the like.

Small amounts of inhibitors are effective to inhibit premature vulcanization. Improvements in processing safety may be observed with 0.05 parts or less of inhibitor per 100 parts rubber. Although there is no upper limit in the amount of inhibitor used, generally the amount does not exceed 5 parts inhibitor per 100 parts rubber. Typically, the amount of inhibitor added is about 0.1 to 2.5 parts per 100 parts rubber with amounts of about 0.2 to 1 part inhibitor per 100 parts rubber being commonly used. Methods for determining scorch times and curing characteristics of rubber stocks which methods were also used in demonstrating this invention are described in U.S. Pat. No. 3,546,185, col. 13, lines 30-53.

DESCRIPTION OF PREFERRED EMBODIMENTS

Example 1

3-Sodium-1,3-thiazolidin-2,4-dione is prepared by charging to a suitable reactor equipped with temperature controlling means and stirring means, 0.2 mole 1,3-thiazolidin-2,4-dione, 0.2 mole sodium methoxide (as 25% solution in methanol) and 150 ml of xylene. The mixture is heated to 110° C. to remove the methanol. To the resulting slurry at 60° C. tert-butane sulfenyl chloride (0.2 mole) in 100 ml of heptane is added dropwise over one hour. By-product sodium chloride is removed by filtration. Upon standing, solid product precipitates from the filtrate. The filtrate is evaporated to recover an oil. The oil is dissolved in toluene and heptane is added to precipitate additional product. 3-(tert-butylthio)-1,3-thiazolidin-2,4-dione, m.p. 70°-72° C., is recovered. Chemical analysis gives 31.28% S and 6.83% N compared with 30.95% S and 6.88% N calculated for $C_7H_{11}NO_2S_2$. NMR analysis shows singlets at 4.1δ and 1.3δ with an area ratio of 2 to 9, respectively.

The process of the invention is demonstrated by using the following natural rubber masterbatch:

| Natural Rubber Masterbatch | |
|---|---|
| | Parts by Weight |
| Smoked sheets | 100 |
| Carbon black | 45 |
| Zinc oxide | 3 |
| Stearic acid | 2 |
| Processing oil | 5 |
| Sulfur | 2.5 |
| N-(1,3-dimethylbutyl)-N'-(phenyl)-p-phenylenediamine | 2 |
| N-(tert-butyl)-2-benzothiazole-sulfenamide | 0.5 |
| Total | 160.0 |

A portion of the masterbatch containing no inhibitor is a control, stock 1. Quantities of test compounds are incorporated into other portions of the masterbatch; N-(tert-butylthio)succinimide in stock 2, 3-(cyclohexylthio)-1,3-thiazolidin-2,4-dione in stock 3, and 3-(tert-butylthio)-1,3-thiazolidin-2,4-dione, an inhibitor of the invention, in stock 4. The properties of the vulcanizable compositions are measured by conventional methods as described above. The results are shown in Table 1.

TABLE 1

| Stock No. | 1 | 2 | 3 | 4 |
|---|---|---|---|---|
| (all parts by weight) | | | | |
| NR masterbatch | 159.5 | 159.5 | 159.5 | 159.5 |
| N-(tert-butylthio)succinimide | — | 0.5 | — | — |
| 3-(cyclohexylthio)-1,3-thiazolidin-2,4-dione | — | — | 0.5 | — |
| 3-(tert-butylthio)-1,3-thiazolidin-2,4-dione | — | — | — | 0.5 |
| Mooney scorch @ 121° C. | | | | |
| $t_5$, minutes | 31.1 | 42.3 | 31.4 | 78.5 |
| % increase in scorch safety | — | 36 | 1 | 152 |
| Rheometer data @ 144° C. | | | | |
| $t_2$ | 8.0 | 8.5 | 9.1 | 14.0 |
| $t_{90}-t_2$ | 14.4 | 41.0 | 16.2 | 29.5 |
| R max. | 64.0 | 60.0 | 66.0 | 62.0 |
| Stress-strain data | | | | |
| 300% modulus, Kg./cm² | 119 | 103 | 117 | 105 |
| Ult. tensile strength, Kg./cm² | 281 | 267 | 285 | 271 |

TABLE 1-continued

| Stock No. | 1 | 2 | 3 | 4 |
|---|---|---|---|---|
| Ult. Elongation, % | 560 | 580 | 580 | 580 |

The data show that 3-(tert-butylthio)-1,3-thiazolidin-2,4-dione is four times more potent as a prevulcanization inhibitor than N-(tert-butylthio)succinimide. The inhibitor of the invention increases the scorch safety 152% compared with only 36% increase in scorch safety for N-(tert-butylthio)-succinimide. The data further show that 3-(cyclohexylthio)-1,3-thiazolidin-2,4-dione exhibits essentially no inhibitor activity. Similar improved results are obtained with other inhibitors of the invention and in synthetic rubber masterbatches.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formula

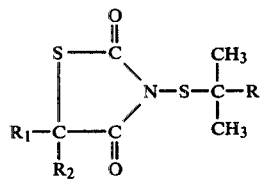

in which R is alkyl of 1-9 carbon atoms, and $R_1$ and $R_2$ independently are hydrogen, alkyl of 1-8 carbon atoms or phenyl.

2. The compound of claim 1 in which R is alkyl of 1-5 carbon atoms, $R_1$ is hydrogen, and $R_2$ is alkyl of 1-4 carbon atoms.

3. The compound of claim 1 in which R is alkyl of 1-5 carbon atoms, and $R_1$ and $R_2$ are alkyl of 1-4 carbon atoms.

4. The compound of claim 1 in which R is alkyl of 1-5 carbon atoms, and $R_1$ and $R_2$ are hydrogen.

5. The compound of Claim 4 in which R is methyl.